United States Patent [19]
Sirén

[11] Patent Number: 4,735,902
[45] Date of Patent: Apr. 5, 1988

[54] STABILIZED COMPOSITION CONTAINING INOSITOLTRIPHOSPHATE

[76] Inventor: Matti Sirén, Casa Camboni, Via al Crespo, CH-6596 Gordola, Switzerland

[21] Appl. No.: 788,830

[22] Filed: Oct. 18, 1985

[30] Foreign Application Priority Data

Oct. 23, 1984 [SE] Sweden ............................ 8405295
Jun. 26, 1985 [SE] Sweden ............................ 8503164
Jun. 26, 1985 [SE] Sweden ............................ 8503165

[51] Int. Cl.$^4$ .............................................. C12N 9/96
[52] U.S. Cl. ..................................... 435/188; 424/85; 424/88; 426/52; 426/654; 514/3; 514/23; 514/44; 514/54; 514/573
[58] Field of Search ............................. 435/188, 183; 252/400.2; 514/970, 3, 23, 44, 573; 426/654, 52; 424/85, 88

[56] References Cited

U.S. PATENT DOCUMENTS 2,723,938  11/1955  Buckwalter et al. ............ 514/103
3,591,665  7/1971   Kimura et al. ............. 252/400.2 X

OTHER PUBLICATIONS

Tomlinson et al., Biochemistry, vol. 1, No. 1, pp. 166–171, (Jan. 1962).
Kerr et al., Archives of Biochemistry and Biophysics, vol. 96, pp. 347–353, (1962).

Primary Examiner—Lionel M. Shapiro
Attorney, Agent, or Firm—Scully, Scott, Murphy & Presser

[57] ABSTRACT

A stabilized composition comprising an organic substrate, such as a pharmaceutical or biological system subject to degradation by oxidation and/or free radicals and a method for production thereof.

14 Claims, No Drawings

STABILIZED COMPOSITION CONTAINING INOSITOLTRIPHOSPHATE

The present invention relates to a stabilized composition comprising an organic substrate, such as a pharmaceutical or biological system subject to degradation by oxidation and/or free radicals, and a method for production thereof.

It is well-known that biological materials and pharmaceuticals often have a rather limited stability even if they are stored in a dark and cold space. Among the pharmaceuticals having such a low stability, insulin, vaccine, hyaluronic acid, intralipid and prostaglandin can be mentioned. In addition, many other organic substrates susceptible to oxidative or free radical degradation are well-known to those skilled in the art and include e.g. fats, oils, ethylenically unsaturated compounds, derivatives and polymers e.g. acrylate compounds and resins, polyvinylacetate, polyvinylpyrrolidone, vinylacetate, vinylpyrrolidone and the like.

It is well-known that the formation of free radicals during storing and/or use of many pharmaceuticals and biological materials causes a degradation of these products. The free radicals namely cause an oxidation, which in its turn results in a degradation of the pharmaceutical or the biological material. Similar mechanisms are responsible for the lack of stability of other organic substrates, such as those mentioned above.

Accordingly, the presence of free radicals can explain why hyaluronic acid for example is effective at application of eyes but not at injection in joints for treatment of rheumatism. Free radicals are formed in the eyes to a slight extent. However, on the other hand, in the joints, free radicals are formed in a considerable amount. Therefore, the hyaluronic acid is broken down or degraded by free radicals in the joint fluids before it has given the desired effect.

In addition to the negative effect on the stability of pharmaceuticals and biological materials, free radicals can also increase the toxicity of said products, which of course is a very serious problem.

A very intensive research effort has been carried out for many years to find an effective and non-toxic stabilizer for organic substrates, such as pharmaceuticals and biological materials. In general, said work has not given the desired result.

In the U.S. Pat. No. 2,723,938 another kind of stabilization than that according to the present invention is disclosed. Thus, according to said patent the use of inositolhexaphosphates (IP$_6$), especially sodium phytate for stabilizing dispersability of aqueous suspensions of insoluble penicillin even after prolonged storage is shown. The use of said sodium phytate is said to insure that brief manual shaking will restore a state of complete and uniform dispersion of the penicillin. However, no effectiveness in stabilization against oxidative degradation caused by free radicals is reported. When compared with IP$_3$ stabilizers of this invention, IP$_6$ is found to be less effective as a stabilizer against degradation of organic substrates. In addition, the use of IP$_6$ is also seriously limited because of the impact on the mineral balance in animals including humans, thus limiting use thereof in compositions to be administered to human hosts.

According to present invention a stabilized composition comprising organic substrates such as pharmaceuticals and biological systems has been provided. The stabilized composition is characterized in that it contains inositoltriphosphate, IP$_3$, in a stabilizing amount.

The appropriate stabilizing amount of IP$_3$ should be determined by routine experimentation to obtain optimum values. For example accelerated aging test can be performed with a test substrate at various levels of IP$_3$ and the optimum level be determined thereby. In general, at least 0.001% by weight of IP$_3$ based on the weight of the composition will provide some beneficial effect. Usually from 0.01-2% by weight will be employed.

The stabilizer is mainly intended to be used against degradation caused by free radicals. Such free radicals can be formed in different ways, for instance by metals, such as iron, aluminium and cadmium, and by radiation.

However, the stabilizer is intended also to be used against degradation caused by oxidation and hydrolysis. The oxidation can be caused by free radicals as mentioned above. However, oxidation can depend on other mechanisms too. Therefore, the invention covers stabilization against oxidation, hydrolysis or radiation, whatever mechanism lies behind said reaction.

The stabilizer can be used for stabilizing many different pharmaceuticals, of which insulin, vaccines, hyaluronic acid, intralipid, prostaglandin and hormones can be mentioned.

Also a lot of different biological materials can be stabilized according to the invention. However, preferably the biological material is selected from DNA, recombinant DNA, RNA, nucleic acids, biological tissue, transplants, carbohydrates, lipids, membranes, proteins, such as enzymes and plasma proteins, culture media for micro-organisms, cell culture media, blood containing substrates, blood for transfusion, nutrient substrates, insemination media, micro-organisms, seeds, plant parts, spores, fruits and food stuffs.

According to one suitable method for the production of IP$_3$ a material containing IP$_6$ is broken down enzymatically with phytase enzyme. The IP$_6$ can be provided either as pure material or in the form of an IP$_6$ containing source, such as wheat bran. Phytase enzyme can be found for instance in plants, seeds and micro-organisms.

By the enzymatic treatment of the IP$_6$ a hydrolysis takes place resulting in a mixture of different lower inositolphosphates, i.e. inositolpentaphosphate (IP$_5$), inositoltetraphosphate (IP$_4$), inositoltriphosphate (IP$_3$), inositoldiphosphate (IP$_2$) and inositolmonophosphate (IP$_1$).

Usually, the hydrolysis is carried out at a temperature of 20°-70° C. and a pH of 4 to 8. The hydrolysis is suitably stopped when the liberation of about 30-60% of the total ester phosphorus has been achieved. At said stage a high proportion of the desired IP$_3$ isomer or isomers has been formed by hydrolysis of the IP$_6$ containing material.

The mixture of inositolphosphates obtained may hereafter be separated by chromatography to isolate the IP$_3$-containing fraction. Preferably, this is made in a column. If the IP$_3$ fraction contains more than one isomer, these isomers are separated in another subsequent chromatographic separation step.

The IP$_3$ can be obtained as a salt or as an acid thereof. The salt form is preferred, since it is easier to produce in pure and concentrated form than the acid.

The salt form of the IP$_3$ isomer is readily obtainable from the acid form using standard procedures. Thus, there can be prepared salts, such as alkali metal and alkaline earth metal salts, e.g. lithium, sodium, potassium, calcium or magnesium. However, also the aluminium, zinc and iron salts are very useful as well as the $NH_4^+$ and organic amine salts. Exemplary amines are triethanolamine, diethanolamine, triisopropanolamine, N,N-dimethyl-2-amino-2-methyl-1-propanol, N,N-dimethylethanolamine, tetrabutylamine and cyclohexylamine. Also other salts might be used. Especially preferred salts are those which are physiologically acceptable.

The invention is not restricted to any particular isomer of $IP_3$. Consequently, all individual isomers of $IP_3$ and mixtures thereof are included in the above definition, $IP_3$. However, preferably the stabilized composition comprises at least one of D-myo-inositol-1.2.6-triphosphate, D-myo-inositol-1.2.5-triphosphate, myo-inositol-1.2.3-triphosphate, D-myo-inositol-1.4.5-triphosphate and L-myo-inositol-1.3.4-triphosphate. Of these isomers D-myo-inositol-1.2.6-triphosphate is preferred.

When using yeast, preferably baker's yeast as a phytase source, only one isomer of $IP_3$ is obtained; namely D-myo-inositol-1.2.6-triphosphate. Especially when the composition comprises pharmaceuticals it is generally preferred to use the isomer or isomers of $IP_3$ in substantially pure form. The stabilizer component of the composition can consist wholly or essentially of $IP_3$.

The stabilizer is non-toxic and very efficient.

Sometimes the composition can also contain a minor amount of other inositolphosphates, especially inositoldiphosphate, $IP_2$ and inositoltetraphosphate, $IP_4$ in addition to $IP_3$. This is particularly the case where seeds, plant parts, spores, fruits and foodstuff are to be stabilized according to the invention. $IP_2$ and $IP_4$ can be presented in acid as well as in salt form.

The $IP_3$-isomers mentioned above have the following formulas:

D-myo-inositol-1.2.6-triphosphate of the formula

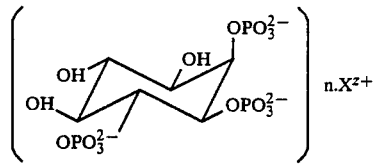

where X is hydrogen, at least one univalent, divalent or multivalent cation, or a mixture thereof, n is the number of ions, and z is the charge of the respectively ion;

D-myo-inositol-1.2.5-triphosphate of the formula

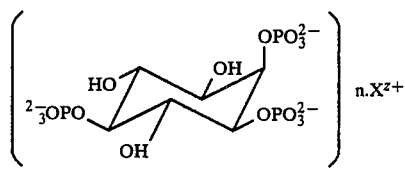

where X, n and z have the above mentioned meaning;
myo-inositol-1.2.3-triphosphate of the formula

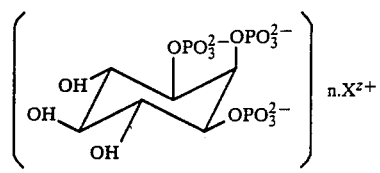

where X, n and z have the above mentioned meaning;
L-myo-inositol-1.3.4-triphosphate of the formula

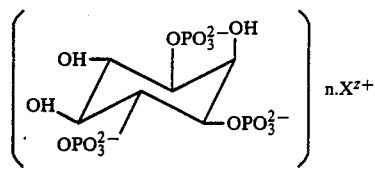

where X, n and z have the above mentioned meaning;
and
D-myo-inositol-1.4.5-triphosphate of the formula

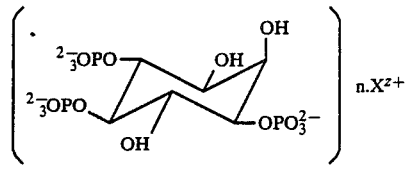

where X, n and z have the above meaning.

In each of the above formulas n ranges between 6 to 1 inclusive and z ranges from 1 to 6 inclusive. Preferably, n is between 3 to 6 inclusive and z is 3, 2 or 1.

The invention will be explained further in detail in connection with the embodiment examples below, of which examples 1–5 show that $IP_3$ prevents or reduces the formation of free radicals. Example 6 illustrates preservation of some fruits and vegetables at the addition of $IP_3$. Example 7 shows that an addition of $IP_3$ to an enzyme gives a remarkable retention of the enzyme activity at storage. Examples 8–14 show production of $IP_3$ and the separation thereof into different isomers.

EXAMPLE 1

An aqueous solution containing 0.3 mM $FeCl_3$, 5.0 mM ethylenediaminotetraacetic acid (EDTA), 50 mM tris (hydroxymethyl)-aminomethan (TRIS) and 1.0 M $NaN_3$ was prepared. In the solution the complex $Fe^{3+}$—EDTA—$N_3$ was formed.

A maximum in absorption of light was detected at the wavelength of 409 nm.

Another aqueous solution containing 0.3 mM $FeCl_3$, 50 mM EDTA and 50 mM TRIS was prepared. In the solution the complex $Fe^{3+}$—EDTA—$H_2O$ was formed. There was no maximum in absorption of light detected at the wavelength of 409 nm.

The above difference in result depends on that $N_3^-$ competitively replaces one water molecule which binds to the $Fe^{3+}$—EDTA—complex. This in turn shows that the $Fe^{3+}$—EDTA—complex has a binding site, which is occupied by a dissociable water-molecule.

It is further known that iron catalyses the formation of hydroxylradicals. For the formation of these the binding of one water molecule to iron is required.

This means that EDTA in the EDTA—$Fe^{3+}$—complex can not inhibit the formation of hydroxyl radicals catalysed by iron.

The above experiment was repeated with the difference that the EDTA was substituted with $IP_3$.

No maximum in absorption was obtained at the wavelength 409 nm.

This result means that the $Fe^{3+}$—complex with $IP_3$ does not bind water. Therefore the formation of free radicals is prevented.

EXAMPLE 2

A reaction mixture consisting of 48 mmol $KH_2PO_4$, 2 mmol Na-ascorbate, 0.1 mmol $H_2O_2$, 0.5 mmol Fe and 1.7 mmol deoxyribose was incubated at 37° C. for 1 hour. Similar reactions mixtures including EDTA 1 mmol or inositol-tri-phosphate ($IP_3$) 1 mmol were similarly incubated. The $IP_3$ used was D-myo-inositol-1.2.6-triphosphate.

After incubation 1.65 ml thiobarbituric acid in 50 mmol NaOH and 1.65 ml 2.8% trichloroacetic acid was added to 2 ml of the reaction mixture. The mixture was heated to 100° C. for 20 minutes and the absorbance at B 532 nm was measured with water as a blank.

The experiments were performed with iron in the form of $Fe^{2+}$ ($Fe(NH_4)SO_4$) and $Fe^{3+}$ ($FeCl_3$). The results were as follows:

Production of free radicals catalyzed by $Fe^{2+}$ and $Fe^{3+}$ in the presence of $IP_3$ or EDTA, expressed as absorbance at 532 nm.

| Group | $Fe^{2+}$ | $Fe^{3+}$ |
| --- | --- | --- |
| Control | 0.76 | 0.79 |
| EDTA | 2.2 | 1.86 |
| $IP_3$ | 0.46 | 0.43 |

These results show that the formation of free radicals in the reaction mixture was diminished by 40% after addition of $IP_3$. The addition of EDTA had an opposite effect. It strongly increased production of free radicals. Thus $IP_3$ was shown to reduce iron-dependent formation of free radicals.

EXAMPLE 3

Lipid peroxidation was studied in lipid micelles. The following reaction mixture was incubated for 2 hours at 37° C.:

0.4 ml Clark-Lubs buffer pH 5.5
0.2 ml phospholipid liposomes
0.1 ml $IP_3$ 0.5–5 mM or 0.1 ml $H_2O$
0.1 ml $Fe^{2+}$ 1 mM or 0.1 ml $H_2O$
0.1 ml $Al^{3+}$ 4 mM or 0.1 ml $H_2O$
0.1 ml $H_2O$ The $IP_3$ was D-myo-inositol-1.2.6-triphosphate. After incubation, 0.5 ml of thiobarbituric acid +0.5 ml 25% HCl was added and the mixture was heated at 100° C. for 15 minutes. 1 ml lubrol PX 1% (Sigma) was added and lipid peroxidation was measured by measuring absorbance at 532 nm. The results were as follows:

| | Concentration, mM | | | Absorbance |
| --- | --- | --- | --- | --- |
| Experiment | $Fe^{2+}$ | $Al^{3+}$ | $IP_3$ | 532 nm |
| 1 | 0.1 | 0 | 0 | 0.36 |
| 2 | 0 | 0.4 | 0 | 0.12 |
| 3 | 0.1 | 0.4 | 0 | 0.89 |
| 4 | 0.1 | 0.4 | 0.5 | 0.36 |
| 5 | 0.1 | 0 | 0.5 | 0.30 |
| 6 | 0.1 | 0 | 0.4 | 0.26 |
| 7 | 0.1 | 0 | 0.2 | 0.29 |
| 8 | 0.1 | 0 | 0.1 | 0.28 |
| 9 | 0.1 | 0 | 0.05 | 0.27 |
| 10 | 0 | 0 | 0 | 0.13 |

$Fe^{2+}$ caused lipid peroxidation (group 1 vs 10). $Al^{3+}$ itself caused no peroxidation (2 vs 10) whereas the combination of $Fe^{2+}+Al^{3+}$ caused much stronger peroxidation than $Fe^{2+}$ alone (1 vs 3). Addition of $IP_3$ completely prevented the interaction between $Fe^{2+}$ and $Al^{3+}$ (3 vs 4). In systems with only $Fe^{2+}$, $IP_3$ caused marked reduction in radical formation (1 vs 5–9).

EXAMPLE 4

Lipid peroxidation was studied in lipid micelles. The following reaction mixture was incubated for 2 hours at 37° C.:

0.4 ml Clark-Lubs buffer pH 5.5
0.2 ml phospholipid liposomes
0.1 ml $IP_3$ 10 mM or 0.1 ml $H_2O$
0.1 ml $Fe^{2+}$ 1 mM
0.1 ml $Cd^{2+}$ 1 mM or 1 ml $Pb^{2+}$ 1 mM or 0.1 ml $H_2O$
0.1 ml $H_2O$ The $IP_3$ was D-myo-inositol-1.2.6-triphosphate. After incubation, 0.5 ml of thiobarbituric acid +0.5 ml 25% HCl was added and the mixture was heated at 100° C. for 15 minutes. 1 ml Lubrol PX 1% (Sigma) was added and lipid peroxidation was measured by measuring absorbance at 532 nm. The results were as follows:

| | Concentration, mM | | | Absorbance |
| --- | --- | --- | --- | --- |
| Experiment | $Cd^{2+}$ | $Pb^{2+}$ | $IP_3$ | 532 nm |
| 1 | 0 | 0 | 0 | 0.63 |
| 2 | 0.1 | 0 | 0 | 1.08 |
| 3 | 0.1 | 0 | 1.0 | 0.73 |
| 4 | 0 | 0.1 | 0 | 1.79 |
| 5 | 0 | 0.1 | 1.0 | 1.32 |

The lipid peroxidation caused by $Fe^{2+}$ (group 1) was strongly increased by Cd (2) and by Pb (4). The effects of both these metals was strongly counteracted by $IP_3$ (3 vs 2 and 5 vs 4).

EXAMPLE 5

Reaction mixtures with the following compositions were incubated for 5 minutes at 37° C.:

| | |
| --- | --- |
| $KH_2PO_4$ buffer pH 7.4 | 20 mM |
| EDTA | 0.1 mM |
| Salicylate | 1 mM |
| Ascorbate | 1 mM |
| $H_2O_2$ | 3.3 mM |
| $Fe^{3+}$ | 0.05 mM |
| $IP_3$ | 0, 2.5, 5 or 10 mM |

The products formed by oxidation of salicylate were quantified with HPLC. The $IP_3$ was D-myo-inositol-1.2.6-triphosphate.

The system studies radical scavenging. Under these reaction conditions, all $Fe^{3+}$ will form complex with EDTA. The Fe—EDTA complex will induce free radical formation, and the ability of IP³ to prevent oxidation of salicylate is studied.

The results of the experiment were:

| Concentration of $IP_3$, mM | Relative amount of salicylate oxidized |
|---|---|
| 0 | 100 |
| 2.5 | 44 |
| 5 | 43 |
| 10 | 19 |

Thus, $IP_3$ is able to act as a radical scavenger, thereby preventing free radical induced damage to other molecules.

EXAMPLE 6

Preservation of some fruits and vegetables at the addition of $IP_3$.

4 g of fresh potatoes, bananas and apples respectively were sliced in 10 pieces each. 5 pieces of the same fruit or vegetable were put into each of 5 different beakers. Three of the beakers were filled with 15 ml of an aqueous solution of $IP_3$ and three additional beakers with 15 ml of an aqueous solution of $IP_6$, in such a way that each 5 pieces of fruit and vegetable were exposed either to pure water or water with $IP_3$ and $IP_6$ respectively. The content of $IP_3$ and $IP_6$ respectively in the water was 1.0 g/l.

The samples were allowed to stand in room temperature for 15 hours. After this period the colour of the samples was inspected and the following data were found:

| | Potato | Banana | Apple |
|---|---|---|---|
| No $IP_3$ added | brown colour | brown colour | brown colour |
| $IP_3$ added | very slight brown | very slight brown | slight brown |
| $IP_6$ added | brown colour | brown colour | brown colour |

The results show that $IP_3$ has a preservative effect on the fruits and vegetables investigated, whereas $IP_6$ has no such effect.

EXAMPLE 7

Enzyme activity at the addition of $IP_3$.

The activity of aldolase with respectively without addition of $IP_3$ was measured as a function of time.

Aldolase degrades fructose-1.6-diphosphate (FDP) to dihydroxyacetonephosphate. This substrate is further reacted by α-glycerophosphatedehydrogenase (GDH) in the presence of nicotinamide adenine dinucleotide, reduced form (NADH) to α-glycerophosphate and nicotinamide adenine dinucleotide, oxidized form (NAD). By measuring the decline of the UV-absorption at 340 nm for the reaction NADH to NAD the activity of the enzyme is determined.

The aldolase was stored at 25° C. and the activity was measured initially and after 72 hours with and without addition of $IP_3$ (4 g/l).

0.5 ul aldolase (A1893 from Sigma Chemical Co, 0.2 U/ml) was mixed with 2.75 ml of a buffer pH 7.5 consisting of 0.10 g $KH_2PO_4$, 0.74 $K_2HPO_4$, 196 $KCH_3CH_2OO$, 50 mg FDP and 8 mg NADH per 100 ml buffer. 1.47 ul GDH was further added and the total volume was diluted to 3.0 ml. The determination of the activity was performed at 30° C.

The following results were obtained:

| Time for storage at 25° C. | No $IP_3$ added | $IP_3$ added | |
|---|---|---|---|
| 0 | 0.12 | 0.12 | decline of absorbance/min |
| 72 hours | 0.05 | 0.07 | decline of absorbance/min |

The results show that the activity of the enzyme was improved by about 40% after addition of $IP_3$ when the activity was determined after 72 hours storage at 25° C.

EXAMPLE 8

Hydrolysis of sodium phytate with wheat phytase and fractionation of a mixture of inositolphosphates.

A 1.6 gram quantity of sodium phytate (from corn, Sigma Chemical Co) was dissolved in 650 ml sodium acetate buffer, pH 5.2. 2.7 gram wheat phytase (EC 3.1.3.26, 0.015 U/mg, from Sigma Chemical Co) was added and the mixture was incubated at 38° C.

The dephosphorylation was followed by determining the inorganic phosphorus released. After 3 hours when 50% inorganic phosphorus was liberated the hydrolysis was stopped by adding 30 ml ammonia to pH 12. A liquid mixture containing inositolphosphates was obtained.

350 ml of the mixture was passed through an ion-exchange column (Dowex 1, chloride form, 25 mm×250 mm) and eluted with a linear gradient of hydrochloric acid (0–0.7 N HCl). Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphate etc. Two fractions with the ratio of phosphorus to inositol of three to one were obtained.

EXAMPLE 9

Fractionation of inositoltriphosphates.

100 ml of the first fraction obtained in Example 8 with a phosphorus/inositol ratio of three to one was neutralized and precipitated as a bariumsalt after addition of 10% excess of 0.1 M bariumacetate solution. 600 mg of the precipitated salt was dissolved in 50 ml 0.18 N hydrochloric acid. The solution was separated on an ion-exchange column (Dowex 1, chloride form, 25 mm×2500 mm) with diluted hydrochloric acid as eluent. Aliquots of eluted fractions were analyzed for phosphorus. Three peaks consisting of isomers of inositoltriphosphates can be seen.

EXAMPLE 10

Structural determination of isomers of inositol-triphosphates with NMR.

The three peaks obtained in Example 9 were analyzed by H-NMR. Data show that the peaks consist of myo-inositol-1.2.6-triphosphate, myo-inositol-1.2.3-triphosphate and myo-inositol-1.3.4-triphosphate respectively.

The second fraction obtained in Example 18 with a phosphorus/inositol ratio of three to one was analyzed by H-NMR. Data show that the fraction consists of myo-inositol-1.2.5-triphosphate.

EXAMPLE 11

Determination of optical isomers of inositol-triphosphates.

20 mg of the compounds determined with NMR according to Example 10 to be myo-inositol-1.2.6-triphosphate and myo-inositol-1.3.4-triphosphate were further chromatographed on a chiral column based on acetylated cellulose (20 mm×300 mm from Merck) with a mixture of ethanol and water as eluent. The fractions were analyzed with a polarimeter. As can be seen each compound consists of one optical isomer, D-myo-inositol-1.2.6-triphosphate and L-myo-inositol-1.3.4-triphosphate respectively.

EXAMPLE 12

Hydrolysis of sodium phytate with baker's yeast and fractionation of a mixture of inositolphosphates.

A 0.7 gram quantity of sodium phytate (from corn, Sigma Chemical Co) was dissolved in 600 ml sodium acetate buffer pH 4.6. 50 gram of baker's yeast from Jästbolaget, Sweden (dry substance: 28%, nitrogen content: 2%, phosphorus content: 0.4%) was added with stirring and incubation was continued at 45° C. The dephosphorylation was followed by determining the inorganic phosphorus released. After 7 hours when 50% inorganic phosphorus was liberated the hydrolysis was stopped by adding 30 ml of ammonia to pH 12. The suspension was centrifuged and the supernatant was collected.

400 ml of the supernatant was passed through an ion-exchange column (Dowex 1, chloride form, 25 mm×250 mm) and eluted with a linear gradient of hydrochloric acid (0–0.7 N HCl).

Aliquots of eluted fractions were completely hydrolyzed in order to determine the contents of phosphorus and inositol. The peaks correspond to different inositolphosphates i.e. a peak with the ratio of phosphorus to inositol of three to one consists of inositoltriphosphates etc.

EXAMPLE 13

Structural determination of isomers of inositoltriphosphate.

The fraction obtained in Example 12 with a phosphorus/inositol ratio of three to one was neutralized and evaporated before analysis with H-NMR. Data show that the peak consists of myo-inositol-1.2.6-triphosphate.

EXAMPLE 14

Determination of optical isomers of myo-inositol-triphosphate.

The same method was used as described in Example 11 with the difference that 10 mg of the compound determined with NMR according to Example 13 was analyzed. As can be seen the compound consists of one optical isomer, D-myo-inositol-1.2.6-triphosphate.

For purposes of further understanding the invention, formulas are given below of some of the IP3-isomers of the invention. Formulas are also given for IP6, IP5, IP4 and IP2.

The lower phosphate-esters of myoinositol are named depending on where the phosphoric acid groups are situated on the inositol ring, with the numbering giving as low position numbers as possible. L and D stand for clockwise and counterclock-wise counting respectively, and are used depending on which result gives the lowest position number. The carbon atom which has an axial phosphoric acid group always has the position number 2. The structural formulae below are simplified to the acid form.

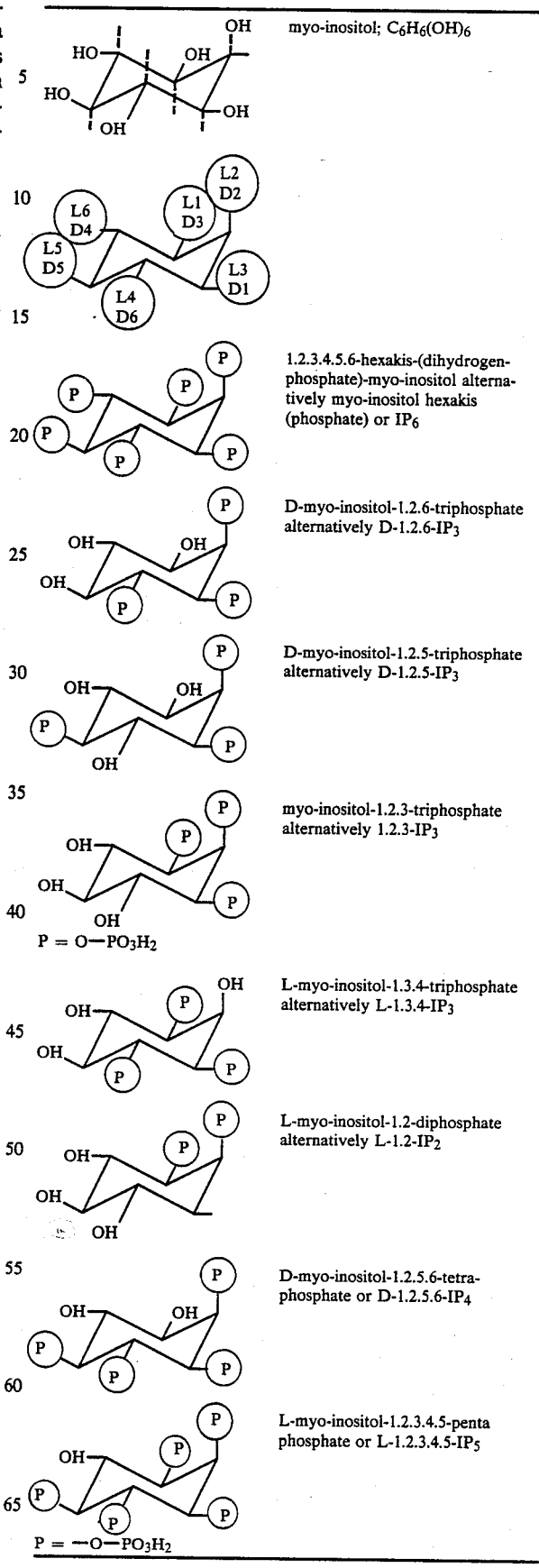

These IP$_3$ compounds are described and prepared in applicant's simultaneously filed patent application Ser. No. 788,829 with the title "Inositoltriphosphate".

I claim:

1. A stabilized composition comprising an organic substrate subject to degradation by oxidation and/or free radicals and between about 0.01% to about 2% by weight, based on the total weight of the composition, of inositol triphosphate (IP$_3$).

2. A composition according to claim 1, wherein the organic substrate is a pharmaceutical or biological system.

3. A composition according to claim 2, wherein the pharmaceutical is selected from the group consisting of insulin, vaccine, hyaluronic acid, intralipid and prostaglandin.

4. A composition according to claim 2, wherein the biological system is selected from the group consisting of nucleic acids, carbohydrates, lipids and proteins.

5. A composition according to claim 1 containing additionally a minor amount of inositoltetraphosphate (IP$_4$) and inositoldiphosphate (IP$_2$).

6. A composition according to claim 1, wherein the IP$_3$ contains at least one of D-myo-inositol-1,2,6-triphosphate, D-myo-inositol-1,2,5-triphosphate, myo-inositol-1,2,3-triphosphate, D-myo-inositol-1,4,5-triphosphate and L-myo-inositol-1,3,4-triphosphate.

7. A composition according to claim 6, wherein the IP$_3$ is a salt, the cation of which is selected from the group consisting of alkali metals and alkaline earth metals.

8. A method of stabilizing an organic substrate which comprises adding between about 0.01% to about 2% by weight of inositol triphosphate (IP$_3$) to an organic substrate subject to oxidation and/or free radical degradation.

9. A method according to claim 8, wherein the organic substrate is a pharmaceutical or biological system.

10. A method according to claim 8, wherein the pharmaceutical is selected from the group consisting of insulin, vaccine, hyaluronic acid, intralipid and prostaglandin.

11. A method according to claim 8, wherein the biological system is selected from the group consisting of DNA, RNA, nucleic acids, biological tissue, carbohydrates, lipids, protein such as enzyme, micro-organisms, seeds, plant parts, spores, fruits and food stuffs.

12. A method according to claim 8, wherein additionally a minor amount of inositoltetraphosphate (IP$_4$) and inositoldiphosphate (IP$_2$) is added.

13. A method according to claim 8, wherein the IP$_3$ contains at least one of D-myo-inositol-1,2,6-triphosphate, D-myo-inositol-1,2,5-triphosphate, myoinositol-1,2,3-triphosphate, D-myo-inositol-1,4,5-triphosphate and L-myo-inositol-1,3,4-triphosphate.

14. A method according to claim 8, wherein the IP$_3$ is a salt, the cation of which is selected from the group consisting of alkali metals and alkaline earth metals.

* * * * *